(12) United States Patent
Christoffersen

(10) Patent No.: US 6,485,593 B1
(45) Date of Patent: Nov. 26, 2002

(54) STERILE DOCKING APPARATUS AND METHOD OF USE

(76) Inventor: Kurt J. Christoffersen, 360 N. 250 East, Millville, UT (US) 84326

( * ) Notice: Subject to any disclaimer, the term of this patent is extended or adjusted under 35 U.S.C. 154(b) by 0 days.

(21) Appl. No.: 09/427,358

(22) Filed: Oct. 26, 1999

Related U.S. Application Data

(60) Provisional application No. 60/105,632, filed on Oct. 26, 1998.

(51) Int. Cl.[7] .............................................. B65H 69/00
(52) U.S. Cl. ........................ 156/158; 156/157; 156/159; 156/304.2; 156/304.6; 156/499; 156/503
(58) Field of Search ........................ 156/82, 157, 158, 156/159, 304.1, 304.2, 304.5, 304.6, 497, 499, 502, 503, 507

(56) References Cited

U.S. PATENT DOCUMENTS

| | | | | |
|---|---|---|---|---|
| 4,737,214 A | * | 4/1988 | Leurink et al. ............. | 156/158 |
| 4,753,697 A | * | 6/1988 | Shaposka et al. ............. | 156/158 |
| 4,793,880 A | * | 12/1988 | Shaposka et al. ............. | 156/158 |
| 4,897,138 A | * | 1/1990 | Shaposka et al. ............. | 156/158 |
| 5,141,592 A | * | 8/1992 | Shaposka et al. ............. | 156/515 |
| 5,156,701 A | * | 10/1992 | Spencer et al. ............. | 156/158 |
| 5,158,630 A | * | 10/1992 | Shaposka et al. ............. | 156/158 |
| 5,209,800 A | * | 5/1993 | Spencer et al. ............. | 156/158 |
| 5,244,522 A | * | 9/1993 | Spencer et al. ............. | 156/158 |
| 5,256,229 A | * | 10/1993 | Spencer ...................... | 156/158 |
| 5,279,685 A | * | 1/1994 | Ivansons et al. ............ | 156/158 |
| 5,674,333 A | * | 10/1997 | Spencer ...................... | 156/64 |
| 5,855,731 A | * | 1/1999 | Spencer ...................... | 156/503 |

* cited by examiner

Primary Examiner—James Sells
(74) Attorney, Agent, or Firm—Brian C. Kunzler

(57) ABSTRACT

An apparatus and method for sterilely coupling two bodies of fluids in fluid communication utilizes a clamp transportable into a sterile enclosure. A pair of tubing segments, each communicating with one of the fluid bodies, is preferably retained in the clamp and transported into the sterile enclosure. The clamp maintains the shape of the tubing segments during the process. Portions of the tubing segments are severed within the enclosure and the remaining ends are heated. The heat may be provided with a hollow disk into which is blown heated air. The ends of the tubing segments are transported out of the enclosure and bonded together while held within the clamps. The clamps prevent deformation of the tubing segments during the process. The process may be partially or fully automated.

20 Claims, 4 Drawing Sheets

STERILE DOCKING APPARATUS AND METHOD OF USE

RELATED APPLICATIONS

This application claims priority to Provisional U.S. Patent Application Serial No. 60/105,632, filed on Oct. 26, 1998, for Sterile Docking Device.

BACKGROUND OF THE INVENTION

1. The Field of the Invention

The present invention relates to devices for coupling two or more bodies of sterile fluids in fluid communication. More specifically, the present invention relates to automated and semi-automated manners of conveniently and efficiently coupling bodies of sterile fluids in fluid communication within a sterile environment.

2. The Relevant Technology

Within the medical, biological, and pharmaceutical industries, the need frequently arises to couple bodies of sterile fluids in fluid communication with each other. In one instance, blood banks and hospitals must often transfer blood, plasma, and other biological fluids between different holders or containers. In a further example, pharmaceutical and research facilities often grow cell cultures within vats or sealed containers. Some manner of accessing to the materials being grown must be provided in order to supply nutrients to the materials, emit waste from the materials, and harvest the materials.

One type of container within which such products are frequently contained is a vinyl or PVC bag. Such bags can be sterilized quite easily by heating the bag at high temperatures or by radiation treatment of the bag. Connections between such containers is frequently made by plastic tubing, which is also typically formed of vinyl, PVC, and other types of synthetic materials. The tubing is also typically sterilized in advance using one of the described methods.

One difficulty arises due to the fact that different containers of fluids such as those mentioned above must be frequently disconnected and reconnected. For instance, in the growth of cell cultures, the cells may be nourished with a serum taken from blood products in which the platelets have been spun out. The serum containers are periodically exhausted and must be exchanged. The exchange of containers must be conducted while maintaining a completely sterile environment. Contamination of the containers can potentially render the contents worthless, and in only a single case, can cause the loss of hundreds of thousands of dollars.

Several manners of coupling such bodies of fluids exist in the prior art. In one example, the sterile fluids are contained in plastic containers. Plastic connectors are used to connect plastic tubing segments emanating from ports in the plastic containers. The tubing segments and plastic connectors are sterilized and kept in sealed paper or plastic bags until use. Nevertheless, making the connections between the tubing segments generally requires human contact. Making such connections requires the expense and inconvenience of maintaining elaborate sterile clean rooms, and any failure to maintain sterility of the process may result in contamination of the sterile fluids.

Semi-enclosed sterile environments have been used in the prior art for making such connections with some success. For example, a laminar flow hood has been used to create a sterile environment for sterilely joining tubing segments. Nevertheless, substantial human contact is still required in the process, and contaminants can be transferred from the operator's hands to the interior of the tubing segments during the process.

A further prior art method currently used for coupling bodies of sterile fluids involves directly bonding the tubing segments together. Under this method, the sterile fluids are located within plastic containers and synthetic tubing segments are bonded to or otherwise connected to the plastic containers. The tubing segments are clamped shut and the edges of the tubing segments are heated until partially melted. The distal tips of the tubing segments are then aligned and held together until the heated plastic of the tubing segments bonds together.

This method of bonding tubing segments while successful to a degree, nevertheless still has its drawbacks. Human contact and its generally unavoidable consequences is still required. Additionally, the process is not carried out in a closed or otherwise sterile environment. Thus, contamination can still occur.

A similar method of joining synthetic tubing segments involves the use of a thin wafer. The wafer is heated by electricity through internal resistance. The wafer is then used to cut the tubing segments. After the tubing segments are cut, the wafer is then used to heat the ends of the tubing segments. The ends of the tubing segments are pinched closed with clamps during the process to avoid contamination and to provide sufficient pressure against the wafer during the heating process. Once heated, the pinched-off tubing segments are held together while the melted synthetic material cools to join the tubing segments. The tubing segments are then unpinched.

Drawbacks with this technique include the fact that the tubing may remain deformed and seal shut during the process. Additionally, due to heating and electricity constraints, only very small, low capacity, tubing is used, such as ⅛ inch I.D. (inside diameter) tubing. This small diameter tubing is often sufficient for purposes such as use in the blood bank industry, but is insufficient for many other purposes. Additionally, this technique is generally not conducted in a sterile environment, and may yet be susceptible to contamination. Furthermore, the technique is difficult and awkward at best when dealing with tubing segments which are filled with fluid during the sealing of the tubing segments together.

Accordingly, a need exists for an improved manner of coupling bodies of sterile fluids in fluid communication. More specifically, such a manner is needed which overcomes the shortcomings of the prior art as described above.

SUMMARY OF THE INVENTION

The present invention solves many or all of the foregoing problems by providing an apparatus and method for joining first and second tubing segments together in sterile fluid communication to enable sterile fluid coupling between two bodies of sterile fluids through the first and second tubing segments. In one embodiment, the apparatus comprises an at least partial enclosure having an interior and is adapted to maintain a sterile environment within at least a substantial portion of the interior.

The apparatus also preferably comprises a tubing clamp adapted to receive the first and second tubing segments therein and mounted to be positionable within the enclosure. Additionally, the apparatus also preferably comprises a heating plate at least partially located within the enclosure. Preferably, the heating plate is provided with one or more heatable surfaces for concurrently heating the first and second tubing segments.

In one embodiment, the heating plate is adapted to sever distal ends of the first and second tubing segments. In an alternative embodiment, the apparatus comprises a cutting blade positionable within the interior to sever distal ends of the first and second tubing segments.

The tubing segments are in one embodiment substantially annular in cross-sectional shape. In this embodiment, the tubing clamp comprises a substantially annular opening adapted to receive the tubing segments without substantially deforming the tubing segments.

A heat source may also be provided, and is preferably connected to and provides heat to the heating device. In one embodiment, the heating plate comprises a hollow disk and the heat source comprises a hot air blower adapted to blow heated air into an interior of the hollow disk. In one embodiment, the cutting surface is also heated by the heat source.

The interior may comprise a heated aseptic environment for maintaining sterility of the tubing segments within the interior. The aseptic environment is preferably maintained by heat from the heat source. The clamps may be at least partially automated, and the clamps may be dynamically mounted upon a track adapted to guide the clamps into and out of the enclosure.

A method of the present invention may involve sterilely coupling first and second fluid bodies in fluid communication. In one embodiment, the method comprises providing the first and second fluid bodies and providing first and second tubing segments, the first tubing segment in fluid communication with the first fluid body and the second tubing segment in fluid communication with the second fluid body.

The method in one embodiment also comprises clamping distal ends of the first and second tubing segments into a selected position relative to an at least partial enclosure having an interior while maintaining a sterile environment within at least a substantial portion of the interior. A subsequent step preferably comprises heating the distal ends of the first and second tubing segments while within the enclosure.

The method also preferably comprises bringing the distal ends of the first and second tubing segments into contact with each other and allowing the distal ends to cool such that the first and second tubing segments bond to each other with a continuous lumen passing through the distal ends. The method may also comprise severing distal ends of the first and second tubing segments while the first and second tubing segments are within the enclosure.

In one embodiment, the first and second tubing segments are automatically transported into the interior once clamped in place for severing and heating, and then automatically transported out of the interior for bonding together. The tubing segments may also be automatically placed against the heating plate, and automatically placed in an adjoining position for bonding together.

BRIEF DESCRIPTION OF THE DRAWINGS

In order that the manner in which the above-recited and other advantages and objects of the invention are obtained will be readily understood, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Figure 2:
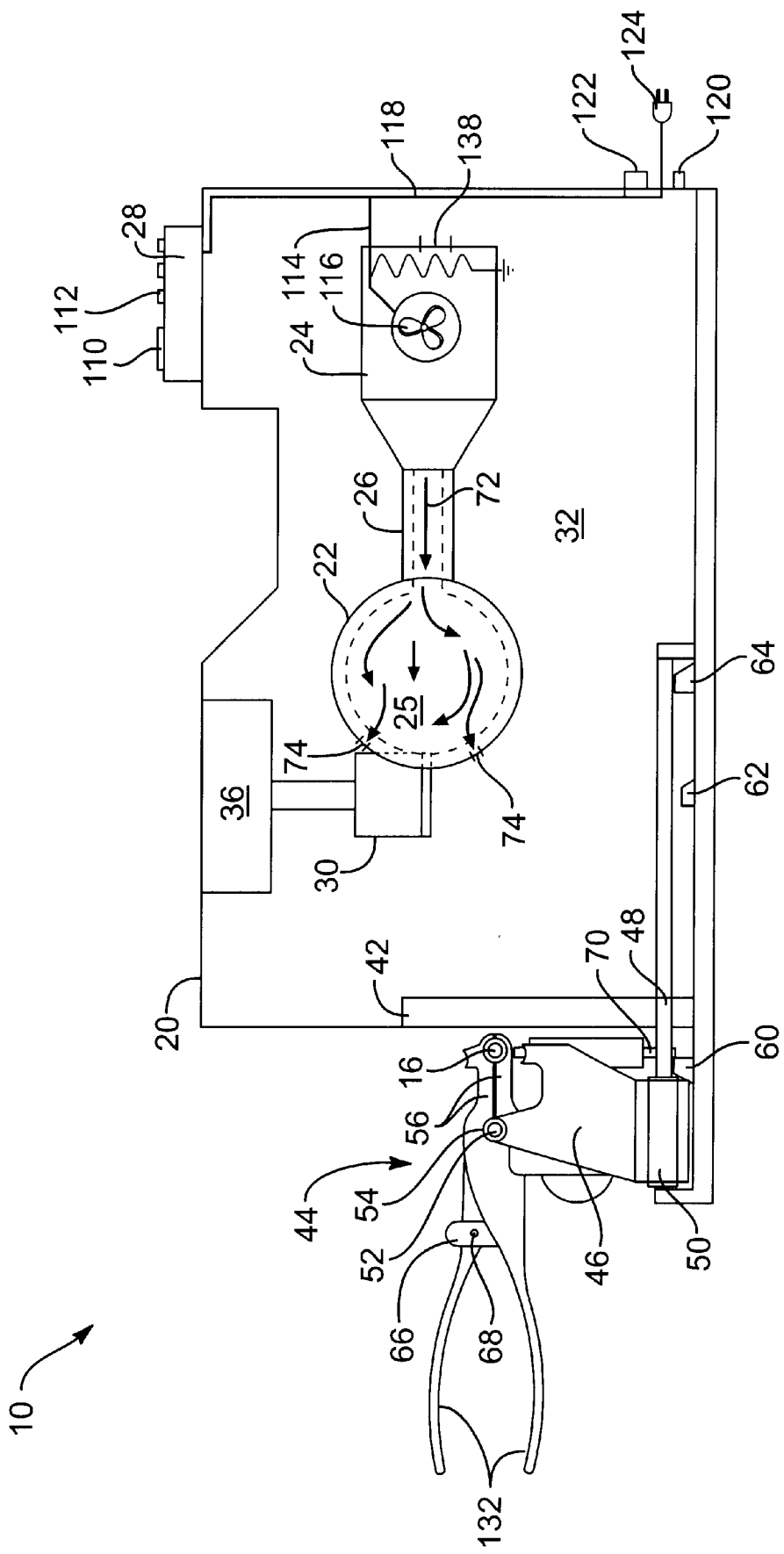
FIG. 2 is a side cut-away view of the sterile docking device of FIG. 1 shown with the tubing clamp carriage in a tubing joining position.
Figure 3:
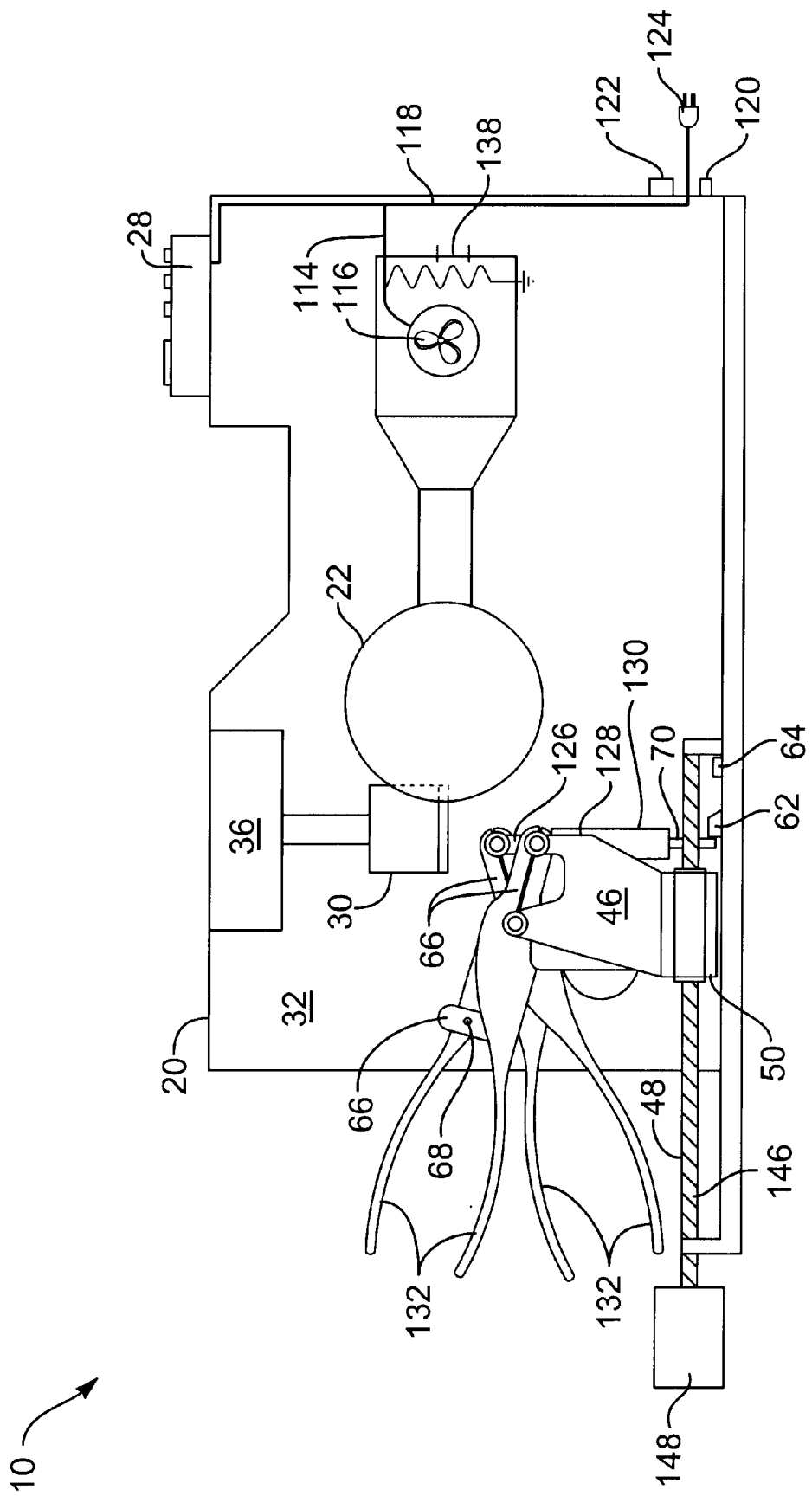
FIG. 3 is a side cut-away view of the sterile docking device of FIG. 1 shown with the tubing clamp carriage in a tubing cutting position.

The present invention is directed to a sterile docking device for joining two tubing segments together within a sterile environment to thereby couple two bodies of sterile fluids in fluid communication. One embodiment of the sterile docking device 10 of the present invention is shown in FIGS. 1 through 3.

Figure 1:
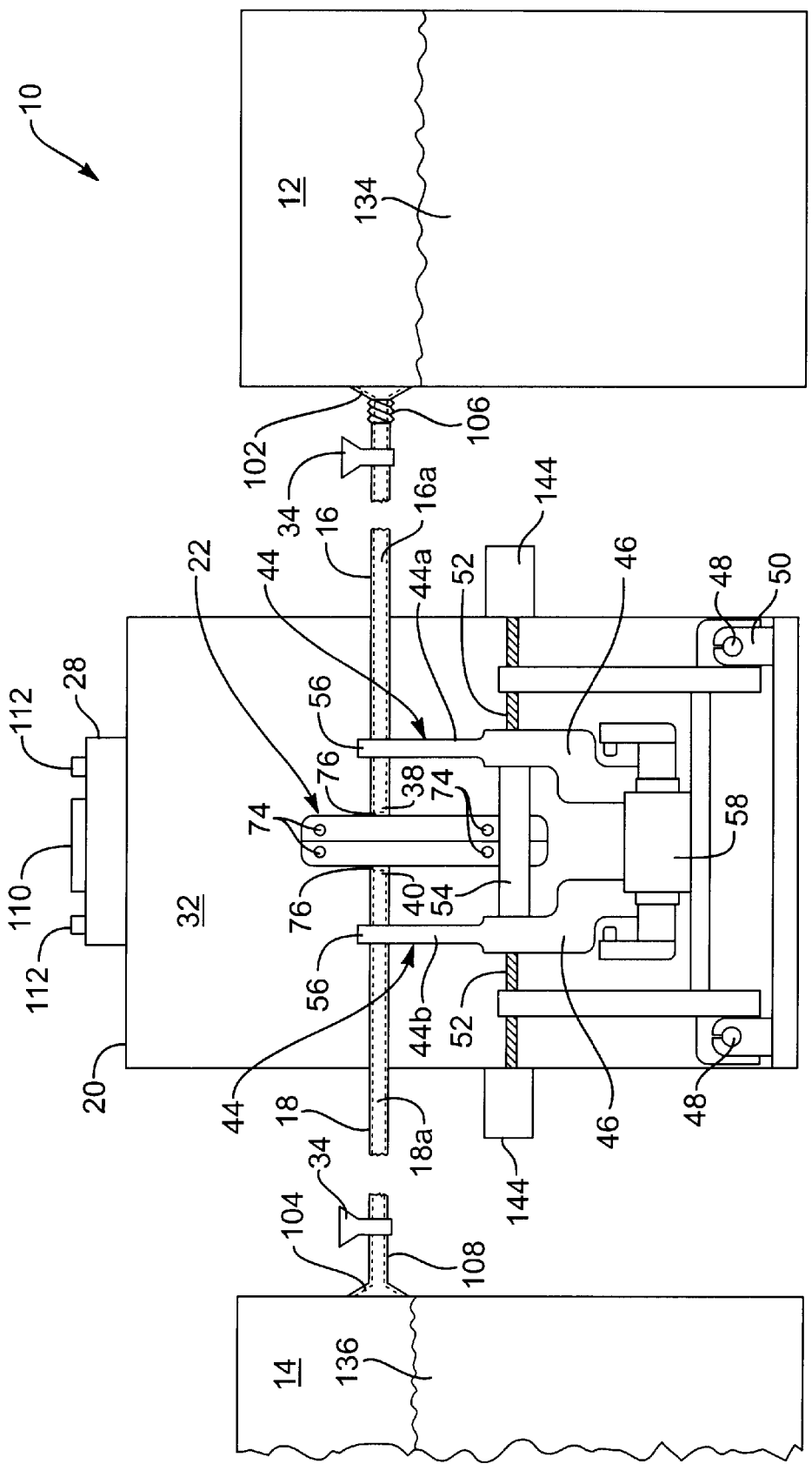
FIG. 1 is a frontal cut-away view of a sterile docking device of the present invention shown with a tubing carriage holder in a tubing heating position.

Referring initially to FIG. 1, one embodiment of a sterile docking device 10 of the present invention can be seen in use in a sterile coupling procedure. Under the present invention, the sterile docking device 10 is preferably used to aseptically join two tubing segments, such as first and second tubing segments 16, 18, together in fluid communication. Once the tubing segments 16, 18 are joined, the sterile fluid containers 12, 14 are coupled in fluid communication such that fluid 134, 136 may be passed between the sterile fluid containers 12, 14 through continuously connected lumens 16a, 18a of the tubing segments 16, 18.

In the depicted embodiments, the tubing segments are ⅜" I.D. Of course, other tubing sizes could also be used, including tubing of greater than ⅜" I.D. The tubing segments 16, 18 are typically much longer than those shown, often in the range of 8 to 10 feet in length. Thus, each tubing segment 16, 18 is shown with a break, representing the indeterminate length of the tubing segments 16, 18. The tubing segments are preferably made of polyolefin material, and may be made of vinyl plastic, PVC, or other suitable moldable synthetic materials.

A presently preferred type of tubing segments 16, 18 is C-Flex tubing available from Consolidated Polymers Tubing Corp. of Largo Fla. One requirement of the tubing material under the present invention is that the tubing segments 16, 18 preferably melt at a relatively low temperature (preferably about 312° F.) and are capable of bonding together in a butt-weld configuration after the ends 38, 40 thereof are partially melted.

In the depicted embodiment, the tubing segments 16, 18 are connected to the containers 12, 14 with ports 102, 104 having ribbed portions 106, 108 over which the tubing segments 16, 18 fit in a snug manner. Of course, the tubing segments 16, 18 could be connected in any suitable manner to the sterile fluid containers 12, 14. The tubing segments 16, 18, are preferably sterilized by autoclaving, gamma radiation or other suitable methods, and are maintained in a sterile condition prior to connection to the sterile fluid containers 12, 14.

In the depicted embodiment, the sterile docking device 10 comprises an at least partial enclosure, such as a housing 20. A heating plate or other heating device, such as a heating disk 22, is preferably located within the enclosure. A heating source, such as a hot air blower 24, is also preferably located within the enclosure and provides heat to the heating disk 22. The heating disk 22 is shown provided with an interior 25 into which hot air from the hot air blower 24 is blown. A passageway 26 connects the hot air blower 24 and the heating disk 22.

Power is provided to the hot air blower 24 in the depicted embodiment through electrical connections 118 from a standard 110 or 220 volt wall plug 124. The standard electricity supply is preferably also rectified into a DC source and provided to the controller 28 and all other automated equipment, such as actuators 38, 58, switches 60, 62, and 64, and any other automating equipment being used. An on-off switch 122 is provided in the depicted embodiment, as is a fuse 120.

A controller 28 controls the output of the hot air blower 24. In the depicted embodiment, the hot air blower also heats a blade 30 and the interior 32 of the housing 20. The controller 28 thus controls the heat of the heating disk 22, the blade 30, and the interior 32. The blade 30 may be used for severing the ends 76 of the tubing segments 16, 18, although, the heating plate could also be used for this purpose.

The interior 32 is preferably maintained at a temperature greater than about 249.8° F. At this temperature, the interior 32 remains aseptic. The hot air exhausts through an opening 42, which provides access to the interior 32. Thus, an area of close proximity around the opening 42 (best seen in FIG. 2) also remains aseptic.

The temperature of the interior 32, the heating disk 22, and the blade 30 may be monitored with sensors and displayed on a display such as a display 110 comprising a 16 digit LED bank. Buttons 112 are provided for operating the controller 28 and setting the desired heat and air output levels. The controller 28 preferably comprises a microprocessor or microcontroller and may be programmed to maintain substantially constant temperatures of the heating disk 22, interior 32, and blade 30. In so doing, the controller may employ a UCD thermostat and controller available from Honeywell Corp. of Minneapolis, Minn. The controller 28 may also be programmed to control automated functions such as the operation of the actuators 38, 58 and any further automation desired to be provided.

Once switched on, power is preferably applied to a heating coil 114 and a fan 116 of the hot air blower 24. Potentiometers or other control devices may be employed by the controller 28 to control the amount of power issued to the resistance coil 114 to thereby control the temperatures of the heating disk 22, blade 30, and the interior 32. Potentiometers may also be used to control the speed of the fan 116. Air is drawn through an air intake 138 from inside the housing 20 and is heated by the resistance coil 114. The heated air is blown by the fan 116 through the passageway 26 into the interior 25 of the heating disk 22. The heated air escapes through openings 74 in the heating disk 22 to heat the interior 32 of the housing 20. One preferred hot air blower 24 is manufactured by Leister Corporation of Kagiswil Switzerland.

As shown in phantom, a portion of the blade 30 is preferably retained within the interior 25 of the heating disk 22. The interior of the heating disk 22 is maintained at an extremely elevated temperature by the hot air from the hot air blower 24. Through heat conductivity, the entirety of the blade 30 is heated to a surface temperature in a range of between about 250° and 400°. Preferably, the temperature is about 325° F. Thus, the blade 30 is enabled to cut through the tubing segments 14, 16 in a cutting operation to be described below without the necessity of being highly sharpened. From this description, it will become apparent that all of the heating disk 22, the blade 30, and the interior 32 (as well as a portion of the exterior proximal the access opening 42) are, in the depicted embodiment, heated by a single heat source, the hot air blower 24. Of course separate heat sources for one or more of these components could be used. Different types of heat sources could also be used, including direct electrical heating or gas heating, but the depicted arrangement is presently preferred.

Also shown in FIG. 1 is a set of tubing clamps 44 (right tubing clamp 44a, left tubing clamp 44b). The tubing segments 16, 18 are shown held within the tubing clamps 44. Preferably, the tubing clamps 44 are provided with cylindrical openings adapted to receive the tubing segments 16, 18 without deforming the tubing segments 16, 18 (Best seen in FIG. 2). In the depicted embodiment, the tubing clamps 44 ride on a carriage 46 which enables movement of the tubing clamps 44 in two dimensions. The carriage 46 preferably rides on track, which in one embodiment comprises a set of carriage rails 48 allowing lengthwise movement of the carriage 46 into and out of the interior 32.

In the depicted embodiment, a ball bearing bushing 50 dynamically connects the carriage 46 to the carriage rails 48 to facilitate the lengthwise movement. In one embodiment, depicted in FIG. 2, the carriage rails are smooth and the lengthwise movement of the carriage 46 is manually propelled.

In a further embodiment, an actuator such as a solenoid or motor is used to control the movement of the carriage 44 along the rails 48. Thus, as depicted in the embodiment of FIG. 3, the rails 48 comprise rotatably mounted and threaded screws 146. In this embodiment, an actuator such as a servo motor 148 is used to rotate the threaded screws 146 in one direction or another. In this embodiment, the carriage 46 is provided with female threads such that rotation of the threaded screws 146 propels the carriage in a selected direction according to the direction of rotation of the threaded screws 146.

A clamp rail 52 is shown in FIG. 1 mounted on the carriage 46 with an orientation transverse to the carriage rails 48. The tubing clamps 44 ride on the clamp rail 52. Mounting the tubing clamps 44 to the clamp rail 52 allows lateral movement of the tubing clamps 44 in a direction orthogonal to the movement provided by the mounting of the carriage 46 on the lengthwise rails 48. In one embodiment, the tubing clamps 44 ride on a ball bearing bushing 54. In this embodiment, the lateral movement is manually propelled.

In an alternative embodiment, the clamp rail 52 is threaded and an actuator, such as a servo motor 144, is used to rotate the threaded clamp rail 52 in one direction or another. In this embodiment, the tubing clamps are female threaded to receive the threaded clamp rail 52 such that rotation of the threaded clamp rail 52 propels the tubing clamps in a selected lateral direction according to the direction of rotation of the threaded clamp rail 52.

As best seen in FIG. 2, the tubing clamps 44 are in one embodiment provided with plier-like jaws 56 which are opened and closed with arms 132. The arms 132, as depicted in FIG. 1, are manually controlled. Nevertheless, one skilled in the art will readily appreciate that automating the opening and closing of the tubing clamps 44 can be readily accomplished and so doing is well within the skill in the relevant art.

A spring clamp 66 is shown mounted to the tubing clamps, and in the depicted embodiment, comprises a flexible plate which springs into place over a pin 68 when the jaws 56 are closed to lock the tubing section 16 within a circular aperture therein. A tight fit of the jaws, and elasticity of the tubing section 16 maintains a tension between the spring clamp 66 and the pin 68. Squeezing the arms 132 slightly and applying lateral pressure on the spring clamp 66 disengages the spring clamp 66 from the pin 68 to allow egress of the tubing section 16.

In the embodiment of FIG. 1, the tubing clamps 44a, 44b are both similarly configured and are thus each operated in the above-described manner to clamp the respective tubing segments 16, 18 within the jaws 56 thereof.

The sterile docking device 10 is preferably mounted or located on a wheeled cart to facilitate easy transportation and access to different locations in which sterile fluid containers 12, 14 may be located. The sterile docking device 10 is also preferably adapted to conveniently plug into any available 110 Volt wall socket with preferably a single electrical plug 124.

A more detailed description of the sterile docking device 10 of FIGS. 1 through 3 will now be given in conjunction with a method of use 150 of FIG. 4. In the method 150, the sterile docking device 10 is used to couple the two depicted sterile fluid containers 12, 14 in fluid communication with each other. In one instance, given by way of example, the first sterile fluid container 12 comprises a biological reactor containing a cell culture 134 being grown for experimental or medicinal use. The second sterile fluid container 14 comprises a serum 136 for sustaining the growth of the cell culture 134.

The serum 136 must be frequently replenished, which requires disconnecting an existing, previously consumed, sterile fluid container 14 and replacing it with a fresh sterile fluid container 14. Accordingly, the sterile docking device 10 is shown in FIGS. 1 through 3 being used in a procedure for connecting the second sterile fluid container 14 to the first sterile fluid container 12 to provide a fresh supply of serum 136.

The method 150 begins as depicted in a start block 152. As depicted in a block 154, a sterile docking device, such as the sterile docking device 10 of FIGS. 1 through 3, is provided. Preferably, the sterile docking device 10 is configured as discussed above. In a subsequent step, depicted by a block 156, the sterile docking device 10 is initialized.

In initializing the sterile docking device 10, the sterile docking device 10 is preferably switched on with the switch 120 and allowed to come up to a preferred operating temperature as discussed above.

As represented by a block 156, the method 150 further involves providing the sterile fluid bodies to be coupled in fluid communication. Typically, this comprises obtaining two fluid bodies such as those discussed above, for which an operator has a need of coupling. As depicted by a block 160, tubing segments are then provided. In the depicted embodiments, this comprises providing the first and second tubing segments 16, 18 and attaching the first and second tubing segments 16, 18 to the first and second fluid containers 12, 14 in the manner described above. Thus, the first tubing segment 16 is preferably in fluid communication with the first fluid container 12, while the second tubing segment 18 is in fluid communication with the second fluid container 14.

In providing the tubing segments, distal ends 38, 40 of the tubing segments 16, 18 are preferably provided, and the tubing segments 16, 18 are preferably sealed off while within a sterile environment. In one embodiment, sealing the distal ends 38, 40 comprises attaching line clamps 34 to the tubing segments 16, 18 as depicted in FIG. 1. The line clamps 34 are preferably attached during the manufacturing of the containers 12, 14 or during the filling of the sterile fluids 134, 136. Additionally, the distal ends 38, 40 may also be sealed shut with line clamps 34 or by bonding.

A further step in the method 150, and particularly in the given example where the first sterile fluid container 12 comprises a biological reactor, may comprise disconnecting an exhausted sterile fluid container 14 in which the nutrients have been consumed. This step is, of course, not necessary when neither of the sterile fluid containers 12, 14 have been previously connected with another sterile fluid container 12, 14.

Prior to disconnecting the old sterile fluid container 14, a line clamp 34 is applied to the tubing segment 16 emanating from the first sterile fluid container 12. Thus, the sterility of the environment is better maintained, leakage is avoided, and any electrical shorting problems are avoided. As discussed, a similar line clamp 34 is preferably also be applied to the tubing segment 18 emanating from the second sterile fluid container 14.

The line clamps 34 may be any suitable clamps for externally sealing off tubing. In one contemplated embodiment, the clamps 34 comprise dual rollers which are automated with actuators and controlled by the controller 28. Valves in the containers 12, 14 or ports 102, 104 could also be used to prevent the flow of sterile fluids during the process.

Figure 4:
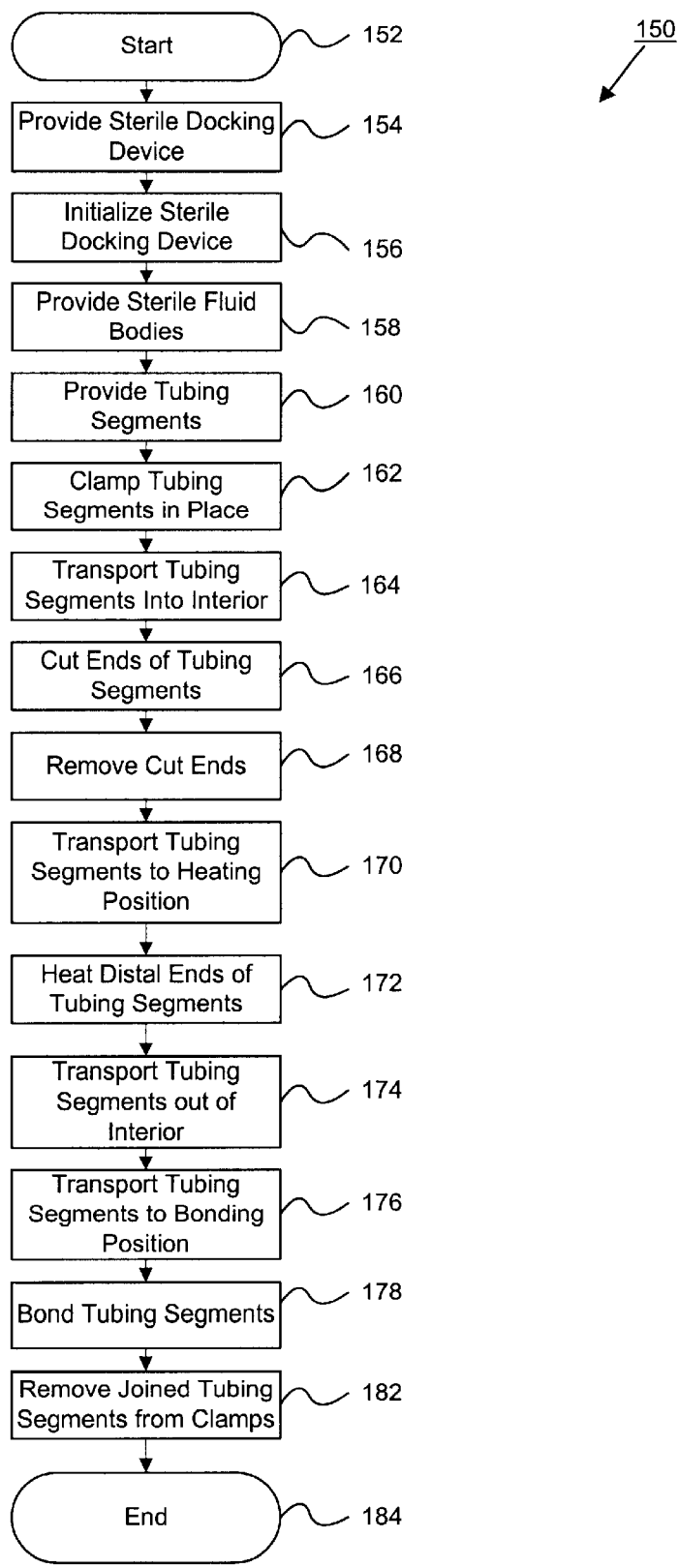
FIG. 4 is a schematic flow chart diagram illustrating one embodiment of a method for sterilely coupling two fluid bodies in fluid communication.

A block 162 of the method 150 of FIG. 4 depicts a step of clamping the tubing segments in place. The preferred arrangement for so doing is best seen in FIG. 2. As shown therein, the carriage 46 and tubing clamps 44 are initially arranged in a loading position outside of the housing 20. Of course, the housing could be extended or provided with doors or cowls so as to maintain the carriage 46 and tubing clamps 44 within a fully enclosed environment.

The spring clamps 66 of each of the two tubing clamps 44a, 44b are disengaged to allow the arms 132 to be separated. Separating the arms 132, in turn, separates the jaws 56. The ends 38, 40 of the tubing segments 16, 18 are then placed within the jaws 56. A portion of each of the ends 38, 40 is allowed to protrude through the jaws 56 to the interior side of the tubing clamps 44 to later be severed by the blade 30. Initially, the two tubing clamps 44a, 44b are offset as seen in FIG. 3, such that the protruding ends 38, 40 of the tubing segments 16, 18 may overlap.

As can be seen in FIGS. 2 and 3, the jaws 56 are each fitted with a semicircular aperture. The apertures form a circular open when the jaws 56 are closed together so as to allow the tubing segments 16, 18 to remain substantially open and un-collapsed when clamped in place within the jaws 56. Of course, the tubing segments 16, 18 could be pinched off during the process, but it is preferred that they remain open.

Once the tubing segments 16, 18 are in place, the jaws 56 are closed. In the depicted embodiment, this is conducted manually by squeezing the arms 132 together. Once again, this operation could also be automated. Under the depicted and described arrangement, human contact is not made with the ends 38, 40 of the tubing segments 16, 18. Furthermore, the heated air emanating from the access opening 42 is sufficiently hot to maintain the sterility and aseptic quality of the tubing segments 16, 18.

As the arms 132 are squeezed together, the spring clip 66 is initially deflected outward by the pin 68, but when the arms 132 reach the closed position, a hole in the center of the spring clip 66 aligns with the pin 68 allowing the pin 68 to protrude into the hole and allowing the spring clip to return to the detente position with the pin 68 firmly engaged therein.

With the tubing segments 16, 18 firmly in place within the jaws 56, the carriage 46 is transported on the carriage rails 48 to the cutting position of FIG. 3, as represented by a block 164 of the method 150. In so doing, the carriage 46, tubing clamps 44, and tubing segments 16, 18 pass through the access opening 42 and into the interior 32 of the housing 20.

In one embodiment represented in FIG. 2, and as referred to above, the carriage transport operation is conducted manually. In the alternative embodiment depicted in FIG. 3, the carriage transport operation is automated with actuators controlled by the controller 28. One such actuator comprises the servo motor 148, male threaded screws 146, and female threaded bushing 50 which operates in the manner discussed above. Programming of the controller 28 to operate the various actuators of the sterile docking device 10 so as to automate the method 150 is considered well within the skill of the relevant art and will not be described herein in further detail.

A block 166 depicts a further step of cutting the distal ends of the tubing segments. This may be conducted in any manner. In one embodiment, the heating plate 22 comprises a blade which is used to cut the tubing segments 16, 18 while held within the tubing clamps 44. In a further embodiment, and as depicted, a cutting surface such as the blade 30 is used.

The tubing segments 16, 18 are preferably of sufficient length to extend from the access opening 42 into place under the blade 30. Nevertheless, the access opening 42 could also be extended towards the blade 30 to allow the tubing segments 16, 18 to protrude out from the lateral sides of the housing 20. Additionally, a hood or cowl may be used to cover the access opening 42 and conserve energy, but the use of a hood or cowl is not required.

In the depicted embodiment, when the carriage 46 reaches the cutting position of FIG. 3, a trip pin 70 at the bottom of a spring-loaded pin bracket 130 trips a switch 62. The switch 62 relays the information that it has been tripped back to the controller 28 (or may directly signal the actuator 36). The actuator 36 is then caused to drop the blade 30 downwards, cutting the ends 38, 40 of the tubing segments 16, 18. An upper tubing support 126 and a lower tubing support 128 provide braces holding the ends 38, 40 in position during the cutting operation. Of course, these operations could also be directly controlled with the controller 28.

The cutting of the ends 38, 40 ensures that the ends 38, 40 and the lumens 16a, 18a passing therethrough are aseptic. Any irregularities in the ends 38, 40 are also removed. Additionally, exposure to the heightened temperatures within the enclosed environment of the housing 32 to which the tubing segments 16, 18 are exposed provides additional insurance of sterility. In the depicted embodiment, the actuator 36 is a solenoid.

As depicted by a block 168, the cut ends of the tubing segments 16, 18 are removed. A tray may be used to catch the portions of the ends 38, 40 once cut by the blade 30. The tray is preferably located at the bottom of the housing 20 and may be removable from the outside of the housing 20.

It may be desired to replace the blade 30 after every operation for greater assurance of sterility, but doing so is not required. If it is desired to replace the blade 30, the blade replacement process may be automated with actuators and coordinated with the controller 28.

A further step represented by a block 170 comprises transporting the tubing segments into a heating position. Thus, in one embodiment, after the distal ends 38, 40 are cut, the pin 70 is temporarily withdrawn into the spring loaded pin bracket 130. The withdrawing of the pin 70 is, in one embodiment, signaled by the controller 28 and effected by an actuator such as a solenoid. Once the pin 70 withdraws, a second actuator 58 (best seen in FIG. 1) is caused by the controller 28 to engage and separate the tubing holders further apart in a lateral direction on the clamp rail 52. This allows the tubing segments 16, 18 to separate so that they may be positioned adjacent the sides of the heating disk 22.

The carriage 46 is subsequently transported further into the interior 32 of the housing. Once again, this transportation operation may be conducted manually or may be accomplished with an actuator such as the servo motor 144. The controller subsequently signals the pin 70 to return to its protruding position. The pin 70 thereafter contacts a second switch 64 when the carriage 46 reaches the tubing heating position of FIG. 1. The controller 28 at this point preferably directs the actuator (either solenoid 58 or server motor 144 depending on the embodiment) to bring the tubing segments 16, 18 inward into contact or close proximity with the heating disk 22.

As depicted by a block 172, the distal ends 38, 40 of the tubing segments 16, 18 are subsequently heated. In the depicted embodiment of FIG. 1, close proximity to the heating disk 22 which is at an elevated temperature of between 350° and 500° F. (preferably about 429° F.) causes the distal ends 38, 40 of the tubing segments 16, 18 to partially melt. It is currently contemplated that the ends 38, 40 are held against the heating disk 22 for a period of about ten seconds.

As depicted by a block 174, the tubing segments 16, 18 are then transported out of the interior. This operation can be manual, or partially or fully automated. In one embodiment, after a sufficient amount of time has passed to sufficiently melt the ends 38, 40 of the tubing segments, but to still maintain the annular shape of the ends 38, 40, the actuator (solenoid 58 or servo motor 144) is again signaled by the controller 28 to separate the tubing clamps 44a, 44b. The carriage 46 is then transported back out of the interior 32 to the position of FIG. 2.

As depicted in a block 176, the tubing segments are then transported to a bonding position. In the depicted embodiment, this comprises directing the actuator (solenoid 58 or servo motor 144) to transport the tubing clamps 44a, 44b together on the clamp rail 52 until the tubing segments 16, 18 are aligned end to end and making contiguous contact around the walls of the lumens 16a, 18a thereof.

As represented by a block 178 of the method 150, the tubing segments are then bonded together. In the depicted embodiment, as the partially melted ends 38, 40 cool, the material of the tubing segments 16, 18 bonds together, effectively butt-welding the tubing segments 16, 18 together. In so doing, the lumens 16a open continuously into each other without occlusions. Because the distal ends 38, 40 are preferably not pinched off in the process, the success rate can be as high as 100 percent.

As depicted in a block 180 of the method 150, the tubing segments 16, 18, now one continuous tubing segment coupling the sterile fluid containers 12, 14 in fluid communication, are removed from the tubing clamps 44 by disengaging the spring clamps 66. If no more tubing segments are desired to be joined at this time, the sterile docking system 10 is switched off with the on-off switch 122 and the method 150 ends, as depicted by a block 182.

The method 150 as described may be partially or fully automated. For instance, the tubing clamps 16, 18 could be used independent of the carriage 46 and the rails 48, 52. The method 150 could also be almost entirely manually conducted. For instance, using the tubing clamps 44 as tongs, or using other grasping devices, even possibly directly by hand, the tubing segments 16, 18 can be entered into the housing 20, pressed against the blade 30 to cut the tubing segments 16, 18 and then pressed against the heating disk 22. Thereafter, the tubing segments can be manually aligned and held together to bond the ends of the tubing segments 16, 18.

When conducting the method 150 manually, it is preferred that an opening in the top of the housing 20 be used together with tongs or tubing clamps 44 freed from the carriage. The interior 32 of the housing 20 is preferably maintained at an elevated temperature as discussed, which is too hot for humans to endure, absent special protective clothing. Thus, with the use of the tongs or tubing clamps 44 (or protective clothing), the critical operations are conducted at the elevated temperatures within the housing 20, maintaining the sterility of the process.

Under the present invention as described herein, the shortcomings of the prior art are substantially overcome. With the use of the sterile docking device 10, large I.D. tubing such as ⅜" I.D. and larger can be used. Due to the substantially closed system and the sterile environment, the joining of the tubing, segments 16, 18 is conducted without contamination and with substantially perfect repeatability. The sterile docking device 10 is substantially or fully automated, providing for lowered instances of operator error. Additionally, as the tubing segments 16, 18 are butt-welded, and done so in an open, non-occluded manner, the coupling of the tubing segments 16, 18 is much less susceptible to failure.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An apparatus for joining first and second tubing segments together in sterile fluid communication to enable sterile fluid coupling between two bodies of sterile fluids through the first and second tubing segments, the apparatus comprising:
    a. an at least partial enclosure having an interior, the enclosure configured to retain heat therein and thereby maintain a sterile environment within at least a substantial portion of the interior of the enclosure;
    b. a tubing clamp adapted to receive the first and second tubing segments therein and mounted to be positionable within the enclosure; and
    c. a heating plate at least partially located within the enclosure, the heating plate having one or more heatable surfaces for concurrently heating the first and second tubing segments.

2. The apparatus of claim 1, wherein the heating plate is adapted to sever distal ends of the first and second tubing segments.

3. The apparatus of claim 1, further comprising a cutting blade positionable within the interior to sever distal ends of the first and second tubing segments.

4. The apparatus of claim 1, further comprising a heat source connected to the heating plate for providing heat to the heating device.

5. The apparatus of claim 4, wherein the heating plate comprises a hollow disk and the heat source comprises a hot air blower adapted to blow heated air into an interior of the hollow disk.

6. The apparatus of claim 1, wherein the tubing segments are substantially annular in cross-sectional shape and the tubing clamp comprises a substantially annular opening adapted to receive the tubing segments without substantially deforming the tubing segments.

7. The apparatus of claim 5, further comprising a cutting surface positionable within the interior to sever the ends of the first and second tubing segments, the cutting surface also heated by the heat source.

8. The apparatus of claim 7, wherein the cutting surface is partially disposed within the hollow disk, such that the heated air within the disk heats the cutting surface.

9. The apparatus of claim 7, further comprising a heated aseptic environment within the interior adapted to maintain sterility of the tubing segments within the interior, the aseptic environment substantially created by heat from the heat source.

10. The apparatus of claim 1, wherein the clamps are dynamically mounted upon a track adapted to guide the clamps into and out of the enclosure.

11. An apparatus for joining first and second tubing segments together in sterile fluid communication to enable sterile fluid coupling between two bodies of sterile fluids through the first and second tubing segments, the apparatus comprising:
    a. an at least partial enclosure having an interior, the enclosure configured to retain heat therein and thereby maintain a sterile environment within at least a substantial portion of the interior of the enclosure;
    b. a tubing clamp adapted to receive the first and second tubing segments therein and mounted to be positionable within the enclosure, the tubing clamp comprising a substantially annular opening adapted to receive the tubing segments without substantially deforming the tubing segments, the tubing clamp dynamically mounted upon a track adapted to guide the clamps into and out of the enclosure;
    c. a hollow disk heating plate at least partially located within the enclosure, the hollow disk heating plate having opposing heatable surfaces for concurrently heating the first and second tubing segments;
    d. a cutting blade positionable within the interior to sever distal ends of the first and second tubing segments, the cutting blade partially disposed within the hollow disk heating plate; and
    e. a hot air blower adapted to blow heated air into an interior of the hollow disk to heat the hollow disk and the cutting blade, the hot air blower also adapted to heat air within the interior of the enclosure to maintain a heated aseptic environment within the interior of the enclosure and thereby maintain sterility of the tubing segments.

12. A method of sterilely coupling first and second fluid bodies in fluid communication, the method comprising:
   a. providing first and second fluid bodies and first and second tubing segments, the first tubing segment in fluid communication with the first fluid body and the second tubing segment in fluid communication with the second fluid body;
   b. clamping distal ends of the first and second tubing segments into a selected position relative to an at least partial enclosure;
   c. heating air within the interior of the enclosure with a heating means and retaining at least a substantial portion of the heated air to maintain a heated aseptic environment within at least a substantial portion of the interior of the enclosure while also using the heating means to heat the distal ends of the first and second tubing segments while the first and second tubing segments arc within the enclosure; and
   d. bringing the distal ends of the first and second tubing segments into contact with each other and allowing the distal ends to cool such that the first and second tubing segments bond to each other with a continuous lumen passing through the distal ends.

13. The method of claim 12, wherein heating the first and second of tubing segments comprises bringing the first and second tubing segments into contact with a heating plate disposed within the enclosure, the heating plate having opposing heated surfaces for concurrently heating the first and second tubing segments.

14. The method of claim 12, further comprising severing the distal ends of the first and second segments of tubing while the first and second segments of tubing are within the enclosure.

15. The method of claim 12, wherein clamping the distal ends comprises placing the distal ends within a clamp mounted to be locatable within the enclosure for positioning the first and second tubing segments within the interior.

16. The method of claim 15, wherein the clamp is dynamically mounted upon a track adapted to guide the clamp into and out of the enclosure.

17. The method of claim 15, wherein the tubing segments are substantially annular in cross-sectional shape and the tubing clamp comprises a substantially annular opening adapted to receive the tubing segments without substantially deforming the tubing segments.

18. The method of claim 12, further comprising transporting the first and second tubing segments into the interior subsequent to clamping the first and second tubing segments into a selected position and prior to heating the first and second tubing segments.

19. The method of claim 12, further comprising transporting the first and second tubing segments out of the interior after heating the first and second tubing segments and prior to bringing the first and second tubing segments into contact with each other.

20. The method of claim 12, wherein clamping the first and second tubing segments in a selected position comprises clamping the first and second tubing segments within a clamp, the clamp dynamically mounted to a track adapted to direct the clamp into and out of the interior, and further comprising automatically transporting the clamp into the interior with the first and second tubing segments clamped therein prior to heating the distal ends and automatically transporting the clamp out of the interior with the first and second tubing segments clamped therein subsequent to heating the distal ends and prior to bringing the distal ends of the first and second segments of tubing into contact with each other.

* * * * *

UNITED STATES PATENT AND TRADEMARK OFFICE
CERTIFICATE OF CORRECTION

PATENT NO. : 6,485,593 B1
DATED : November 26, 2002
INVENTOR(S) : Kurt J. Christoffersen It is certified that error appears in the above-identified patent and that said Letters Patent is hereby corrected as shown below:

Title page,
Item [57], ABSTRACT,
Line 2, "utilizes" should read -- utilize --.

Column 6,
Line 8, should have no new paragraph.

Column 8,
Line 27, "also be" should read -- also --.
Line 57, "open" should read -- opening --.

Column 13,
Line 25, "second of tubing" should read -- second tubing --.

Signed and Sealed this

Twenty-fifth Day of February, 2003

JAMES E. ROGAN
*Director of the United States Patent and Trademark Office*